US010099185B2

(12) United States Patent
Logue et al.

(10) Patent No.: US 10,099,185 B2
(45) Date of Patent: Oct. 16, 2018

(54) ENHANCED ENCLOSURES FOR ACOUSTICAL GAS CONCENTRATION SENSING AND FLOW CONTROL (71) Applicant: Veeco Instruments Inc., Plainview, NY (US)

(72) Inventors: Ray Logue, Henderson, NV (US); Don Sirota, Poughkeepsie, NY (US); Karthik Karkala, Wappinger Falls, NY (US); Eric Armour, Pennington, NJ (US); Christopher A. Morath, Basking Ridge, NJ (US); Arindam Sinharoy, Furlong, PA (US)

(73) Assignee: Veeco Instruments Inc., Plainview, NY (US)

( * ) Notice: Subject to any disclaimer, the term of this patent is extended or adjusted under 35 U.S.C. 154(b) by 341 days.

(21) Appl. No.: 14/822,410

(22) Filed: Aug. 10, 2015

(65) Prior Publication Data

US 2016/0041126 A1 Feb. 11, 2016

Related U.S. Application Data

(60) Provisional application No. 62/035,988, filed on Aug. 11, 2014, provisional application No. 62/100,285, filed on Jan. 6, 2015.

(51) Int. Cl.
*G01N 29/024* (2006.01)
*B01F 5/06* (2006.01)
(Continued)

(52) U.S. Cl.
CPC ......... *B01F 5/0602* (2013.01); *G01N 29/024* (2013.01); *G01N 29/222* (2013.01);
(Continued)

(58) Field of Classification Search
CPC .. G01N 29/024; G01N 29/22; G01N 29/4429; G01N 29/222; G01N 2291/102;
(Continued)

(56) References Cited

U.S. PATENT DOCUMENTS 5,603,169 A 2/1997 Kim
6,116,080 A 9/2000 Logue et al.
(Continued)

FOREIGN PATENT DOCUMENTS

EP 0730151 A2 9/1996

OTHER PUBLICATIONS

Fisher et al "On an Absolute Criterion for Fitting Frequency Curves," Messenger Mathematics, 41, pp. 155-160, 1912.
(Continued)

*Primary Examiner* — Manish S Shah
*Assistant Examiner* — Rose M Miller
(74) *Attorney, Agent, or Firm* — Patterson Thuente Pedersen, P.A.

(57) ABSTRACT

Mass-transfer rate control arrangement and method in which a process precursor mixture is produced containing carrier gas and a process precursor gas. A quantity of the process precursor present in the process precursor mixture is acoustically sensed to produce a sensor output. A dilution gas is provided and the process precursor mixture and the dilution gas are separately conveyed to a dilution point, at which a diluted mixture of the dilution gas and the process precursor mixture is achieved. A relative flow rate of the carrier gas and the dilution gas is automatically controlled in response to the sensor output such that the diluted mixture at the dilution point has a prescribed mass transfer rate of the precursor gas.

20 Claims, 6 Drawing Sheets

(51) Int. Cl.
  *G01N 29/22* (2006.01)
  *G01N 29/44* (2006.01)
  *G05D 11/13* (2006.01)

(52) U.S. Cl.
  CPC ....... *G01N 29/4436* (2013.01); *G05D 11/138* (2013.01); *G01N 2291/021* (2013.01); *G01N 2291/02809* (2013.01); *G01N 2291/102* (2013.01)

(58) Field of Classification Search
  CPC ... G01N 2291/021; G01N 2291/02809; G01N 30/32; G01N 29/4436; F24H 1/20; A61M 5/142; B81B 3/00; G05D 11/138; B81C 1/00; B01F 5/0602
  USPC .......................................................... 73/587
  See application file for complete search history.

(56) References Cited

U.S. PATENT DOCUMENTS

| | | | |
|---|---|---|---|
| 6,192,739 B1 | 2/2001 | Logue et al. | |
| 6,199,423 B1 | 3/2001 | Logue et al. | |
| 6,279,379 B1 | 8/2001 | Logue et al. | |
| 6,561,498 B2 | 5/2003 | Tompkins et al. | |
| 2002/0124662 A1* | 9/2002 | Suzuki | G01F 1/662 73/861.28 |
| 2007/0221127 A1 | 9/2007 | Tran et al. | |
| 2008/0060364 A1* | 3/2008 | Watanabe | F25B 9/145 62/6 |
| 2010/0322604 A1 | 12/2010 | Fondurulia et al. | |
| 2013/0221457 A1 | 8/2013 | Conti et al. | |
| 2014/0060153 A1 | 3/2014 | Logue et al. | |
| 2014/0114282 A1 | 4/2014 | Gray | |

OTHER PUBLICATIONS

Trees et al "Detection and Estimation Theory," John Wiley & Sons, Inc., New York, 1968.

Application and File History for U.S. Appl. No. 13/705,650, filed Dec. 5, 2012, Inventors Logue et al.

International Search Report and Written Opinion, for PCT/US2015/044423, dated Oct. 28, 2015, 17 pages.

\* cited by examiner

ENHANCED ENCLOSURES FOR ACOUSTICAL GAS CONCENTRATION SENSING AND FLOW CONTROL

CROSS-REFERENCE TO RELATED APPLICATIONS

This application claims the benefit of priority of U.S. Provisional Patent App. Nos. 62/035,988 (filed 11 Aug. 2014) and 62/100,285 (filed 6 Jan. 2015), the contents of which are incorporated by reference in their entirety.

FIELD OF THE DISCLOSURE

The present disclosure is directed generally to acoustical sensors and more specifically to acoustical sensors for the sensing of constituent concentration levels in a process medium.

BACKGROUND OF THE DISCLOSURE

Acoustical sensors can be utilized in chemical vapor deposition (CVD) systems to determine concentrations of select constituents. The basic operating principle of these instruments is to infer the concentration of the select constituent from differences in the time-of-flight of an acoustical signal through a test medium compared with that of a pure carrier. For example, in metalorganic CVD (MOCVD) systems, acoustical sensors find utility in the determination of bis-cyclopentadienylmagnesium (Cp2Mg) concentrations. Use of acoustical sensors in CVD applications generally are described, for example, at U.S. Pat. Nos. 6,116,080, 6,192,739, 6,199,423, and 6,279,379, and at U.S. patent application Ser. No. 13/705,650, the disclosures of which are hereby incorporated by reference herein except for express definitions contained therein.

Problems can arise when it is desired to accurately detect low concentrations of the constituent. A system that is tailored to address the challenges of low concentration detection in acoustical sensing systems would be welcomed.

SUMMARY OF THE DISCLOSURE

In various embodiments of the disclosure, the acoustical path length within the acoustical sensor in increased, thereby increasing the time-of-flight through the test medium and making the standard deviation of the time delay measurement a smaller percentage of the difference in the time-of-flight between a pure carrier and a nominal source/carrier mixture (e.g., a Cp2Mg and $N_2$ carrier gas mixture). In one embodiment, the acoustical path length is increased threefold over the path length found in conventional acoustic sensors. In certain embodiments, measures are taken to avoid parasitic loss of constituent vapors that otherwise condense out of the test stream. In other embodiments, the standard deviation of the time delay measurement is decreased by increasing the number of cycles in the transmitted signal, thereby increasing the total signal energy.

In a related aspect, in addition to increasing the acoustical path length and reducing parasitic condensation losses, the measurement system is enclosed in a heated enclosure. The heated enclosure can be of substantially elevated temperature so that the lines that direct the slip stream into the acoustic sensor remain above the condensation point of the constituent/carrier gas mixture. In this way, none of the constituent is condensed out of the mixture, so that the full concentration available from the gas source is made available to the acoustical sensor.

Prior attempts at preventing condensation of the constituent gas have typically involved the use of a heat trace coupled to the plumbing that routes the incoming slip stream to the acoustical sensor. The heat trace approach posed at least two problems: (1) "cold spots" can develop on the plumbing due to non-uniform wrapping of the trace (e.g., at elbows or around support structures) or where contact between the trace and the plumbing is less than ideal; and (2) the energy delivered the gas can cause the temperature exiting the plumbing and entering the acoustical sensor to be greater than or less than the acoustical sensor, thereby causing thermal gradients within the acoustical sensor.

In various embodiments disclosed herein, a the plumbing between the inlet and the acoustical sensor within the heated enclosure is sized so that the temperature of the incoming gas is effectively at thermal equilibrium with the temperature of the components within the heated enclosure by the time the gas reaches the acoustical sensor. Thus, the differences between the incoming mixture and the acoustical sensor—and the attendant introduction of temperature gradients in the system—can be reduced or eliminated. Furthermore, the heated enclosure can eliminate cold spots that are present in heat trace systems, thereby reducing or eliminating the formation of condensation.

An issue that can arise when increasing the path length through which the acoustic signal is transmitted is an increased sensitivity to distortions caused by thermal gradients. Thermal gradients within the acoustical sensor can cause an otherwise parallel relationship between the acoustical transformers (i.e., transducers) of the transmitter and the receiver to become slightly skewed or cause the transformers to become slightly non-planar. Increasing the path length of the acoustic sensor also increases the effect that these distortions have on the quality of the received signal. Accordingly, to obtain the greater benefit from increasing the path length of the acoustic sensor, certain disclosed embodiments are tailored to reduce the thermal gradients in the system.

One source of thermal gradients is "thermal stratification." Thermal stratification is a natural phenomenon that naturally occurs within a heated enclosure; warmer gases tend to rise within the enclosure, so that the gas temperature at the top of the enclosure is warmer than the gas temperature at the bottom of the enclosure. Such stratification can introduce thermal gradients along the vertical length of the acoustical sensor.

Conventionally, the answer to thermal stratification is to mix the air with a fan. Such fans are known in the art as "destratification fans." However, the use of a fan can be precluded in CVD environments because of the presence of explosive or flammable agents; the motor that drives the fan provides an ignition source that can pose a danger.

Accordingly, certain embodiments of the disclosure are configured to introduce mixing of the gases within the heated enclosure without the use of a fan. In one embodiment, the mixing is accomplished by leaving at least a portion of a vertical member of the enclosure unheated, referred to herein as an "unheated portion" or "unheated surface." The unheated portion tends to run cooler than the heated portions of the enclosure, so that gas coming in contact therewith is also cooled relative to the average temperature of the gas within the enclosure. The cooler, denser gas cascades downward over the unheated surface and into the central portion of the enclosure. There, the gas is reheated and rises to the top of the enclosure away from the unheated portion. By this mechanism, a natural convection is established within the enclosure which mixes the gases and provides destratification. The gradient introduced by the natural convection loop can be substantially less than the gradient otherwise introduced by thermal stratification, resulting in a more thermally uniform gas temperature within the enclosure.

Structurally, an apparatus for acoustically determining a property of a test medium is disclosed in one embodiment, the apparatus comprising an enclosure including a base and a cover, the base and the cover cooperating to define a chamber. In this embodiment, an acoustical sensor is mounted to the base, the acoustical sensor including a first acoustical transformer defining a first exposed face and a second acoustical transformer defining a second exposed face. The first exposed face and the second exposed face are substantially parallel and adapted for contact with the test medium and defining a gap therebetween. At least one heating element is operatively coupled with the enclosure. In this embodiment, a first portion of the enclosure is directly coupled with the at least one heating element, the first portion being vertically oriented. The at least one heating element can substantially surround the acoustical sensor. A second portion of the enclosure is not directly coupled with the at least one heating element, the second portion being vertically oriented and opposing the first portion of the enclosure. In one embodiment, the "first portion" of the enclosure is the base.

In one embodiment, the second portion of the enclosure can be operatively coupled to a cooling device (e.g., a plurality of cooling fins); in other embodiments, the second portion of the enclosure is cooled by natural convection to the ambient surroundings.

In various embodiments, the enclosure substantially defines a rectangular box, the cover defining a top portion, a bottom portion, a first side portion, a second side portion and a third side portion, the second side portion being adjacent to and disposed between the first side portion and the third side portion. In one embodiment, the second portion of the enclosure is the second side portion. The acoustical sensor can be oriented so that the first exposed face of the first acoustical transformer and the second exposed face of the second acoustical transformer face horizontally.

In some embodiments, the gap is greater than 12 mm and less than 50 mm. In one embodiment, the gap is approximately 15 mm; in another embodiment, the gap is approximately 30 mm.

In various embodiments of the disclosure, a method of maintaining an acoustical sensor at a substantially uniform temperature is disclosed, comprising:

providing an acoustical sensor mounted within an enclosure, the acoustical sensor including first and second acoustical transformers that are substantially parallel to each other and adapted for contact with a test medium, the first and second acoustical transformers defining a gap therebetween;

providing a heating system adapted to apply heat to portions of the enclosure, the portions substantially surrounding the acoustical sensor; and providing a set of instructions on a tangible medium, the instructions comprising:

heating portions of the enclosure that substantially surround the acoustical sensor;

cooling a substantially vertical portion of the enclosure to induce a recirculation of a gas within the enclosure, the recirculation causing destratification of the gas within the enclosure.

In one embodiment, the step of cooling a substantially vertical portion of the enclosure includes free convection between the substantially vertical portion of the enclosure and ambient surroundings. The step of heating portions of the enclosure include controlling the temperature of the portions to a set point that is at least 20° C. greater than an ambient temperature that surrounds the enclosure.

In certain embodiments, the destratification of the gas causes a spatial temperature variation of the gas within the enclosure to be within a predetermined value. In one embodiment, the predetermined value of the spatial variation of the gas within the enclosure is less than 0.5° C.

In a related aspect of the invention, an apparatus for acoustically determining a property of a test medium is provided in which a first acoustical transducer is electrically coupled with a transmitter circuit constructed to actuate the first acoustical transducer by a first generated signal having a frequency of between 2 and 3 MHz and a duration of between 15 and 50 cycles to produce a first acoustical signal directed to travel through the gap between the transducers. In one particular embodiment, a 30-cycle duration is used. The second acoustical transducer is electrically coupled with a receiver circuit constructed to produce a first received signal from the first acoustical signal. The receiver circuit is electrically coupled to a digitizing circuit configured to sample the first received signal at a sampling rate of between 20 and 100 samples per cycle to produce a first received digital signal. In a particular embodiment, 32 samples per cycle are taken.

The digitizing circuit is electrically coupled to a controller circuit that includes a processor and a non-transitory data storage medium containing instructions that, when executed, cause the processor to apply a maximum-likelihood function to the first received digital signal and to a reference digital signal, and to determine a time delay between a feature of the first received digital signal and a feature of the reference digital signal. The features of the received digital signal and reference digital signal being compared can be a peak of the respective maximum-likelihood functions of these digital signals. The time delay is indicative of the property of the test medium being analyzed. This property can be a material concentration, pressure, or other measurable property.

In one type of measurement arrangement, the reference digital signal is produced from the first generated signal. In another measurement arrangement, the reference digital signal is produced by digitizing an earlier portion of the first acoustical signal, with the first received digital signal actually being produced from a later-received portion of the first acoustical signal that is an echo of the earlier portion.

An exemplary application for an acoustical sensing arrangement according to a related aspect of the invention is directed to a mass-transfer rate control arrangement. The arrangement includes a carrier gas source, and a carrier gas mass flow regulator arranged to regulate a rate of flow of carrier gas from the carrier gas source. Also includes is a process precursor source, including a precursor vessel having an inlet in fluid communication with the carrier gas source via the carrier gas mass flow regulator, and an outlet arranged to convey a mixture of the process precursor and the carrier gas. An acoustical sensor is in fluid communication with the outlet, and includes a chamber arranged to convey a flow of the mixture through it. The acoustical sensor further comprises an electrical signal generator constructed to generate an electrical signal representing a quantity of the process precursor present in the mixture flowing through the chamber.

The arrangement further includes a dilution gas source, and a dilution gas mass flow regulator arranged to regulate a rate of flow of the dilution gas from the dilution gas source. The dilution gas source is in fluid communication with the outlet of the precursor vessel via the dilution gas mass flow regulator, and the fluid communication of the dilution gas source and the outlet of the precursor vessel includes a dilution point at which a diluted mixture of the dilution gas and the process precursor-carrier gas mixture is achieved.

A controller is electrically coupled with at least one of the carrier gas mass flow regulator, the dilution gas mass flow regulator, and with the acoustical sensor. The controller is configured to adjust at least one of the carrier gas mass flow regulator and the dilution gas mass flow regulator in response to the electrical signal from the acoustical sensor such that the diluted mixture at the dilution point has a prescribed mass transfer rate.

In a related aspect of the invention, a method for controlling a mass-transfer rate within a process gas mixture includes providing a carrier gas, providing a process precursor gas, and producing a process precursor mixture containing the carrier gas and a process precursor gas. Further, the method includes acoustically sensing a quantity of the process precursor present in the process precursor mixture to produce a sensor output. A dilution gas is provided. According to the method, the process precursor mixture and the dilution gas are separately conveyed to a dilution point, at which a diluted mixture of the dilution gas and the process precursor mixture is achieved. A relative flow rate of the carrier gas and the dilution gas is automatically controlled in response to the sensor output such that the diluted mixture at the dilution point has a prescribed mass transfer rate of the precursor gas.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Figure 1:
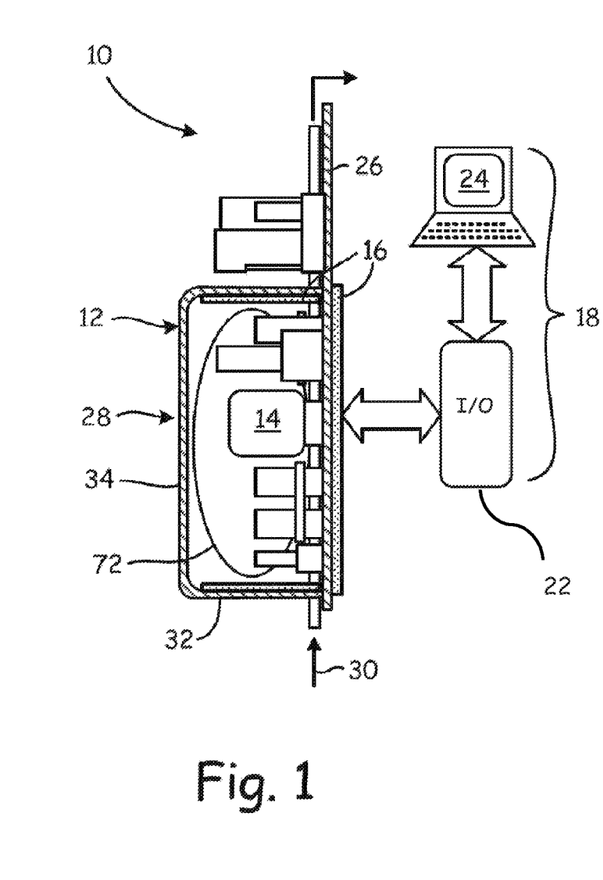
FIG. 1 is a schematic of a heated enclosure and destratification system in an embodiment of the disclosure.

Referring to FIG. 1, a destratification system 10 is depicted in an embodiment of the disclosure. The destratification system 10 includes an enclosure 12 that contains an acoustical sensor 14, with a plurality of heating elements 16 operatively coupled to the enclosure. The heating element(s) can be controlled by a control system 18. In one embodiment, the control system 18 includes an input-output (I/O) interface 22 that is controlled by a microprocessor-based controller 24, such as a computer. The I/O interface 22 can include one or more temperature controllers (not depicted) for controlling the temperature(s) of the heating elements 16, and can also include temperature sensor signal conditioners (not depicted) for acquiring temperature readings for monitoring and/or logging by the controller 18.

Figure 2:
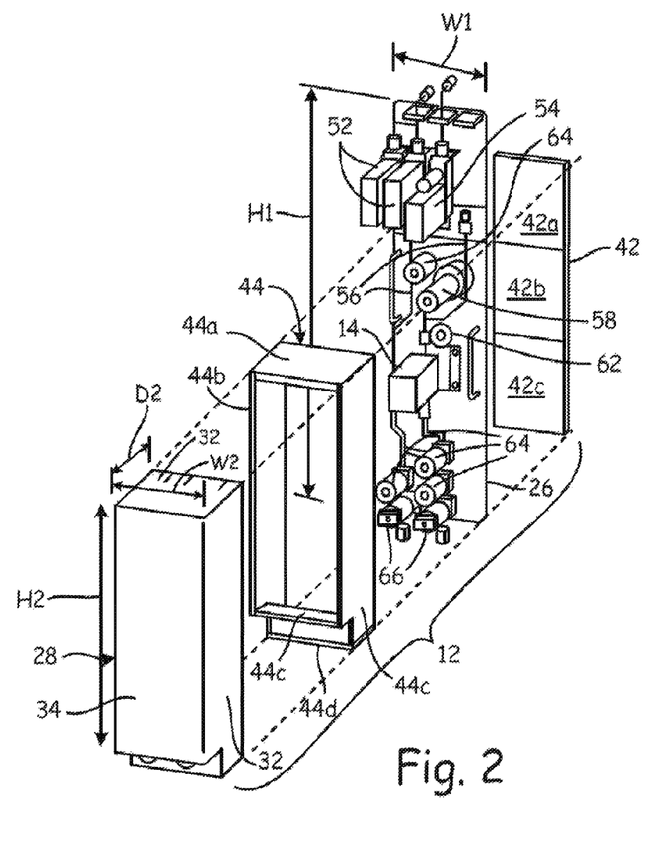
FIG. 2 is a semi-exploded view of the heated enclosure of FIG. 1 in an embodiment of the disclosure.

Referring to FIG. 2, the enclosure 12 is depicted in a disclosed embodiment. The enclosure 12 can comprise a base 26 and a cover 28, the base 26 serving as a mounting plate for the acoustical transformer 14 and for various appurtenances used in the control and conditioning of gases 30 that pass through the acoustical transformer 14. Also in the depicted embodiment, the cover 28 can be characterized as including perimeter portions 32 that are adjacent the base and one or more opposing portion(s) 34 that are opposite the base 26.

The plurality of heating elements 16 are operatively coupled with the enclosure 12. In one embodiment, the heating elements 16 include a base heating element 42 and a cover heating element assembly 44. The cover heating element assembly 44 can comprise a single heating element substantially formed to the shape of the perimeter portions of the cover (not depicted), or can comprise a plurality of heating elements (e.g., 44a through 44e) that are pieced together to substantially canvas the perimeter portions of the cover.

At least part of at least one vertical portion of the enclosure, referred to herein as an "unheated portion(s)," is not directly coupled with a heat source. In the depiction of FIG. 2, the unheated portion is the opposing portion 34 of the cover 28. In one embodiment, the unheated portion(s) (e.g., opposing portion 34) are also not thermally insulated, thereby further promoting the cooling of the unheated portion(s) by the gases that are ambient to the enclosure 12.

In the embodiment of FIG. 2, the cover heating element assembly 44 is depicted as being inserted inside the cover 28, i.e., as being operatively coupled with the interior faces of the cover 28. Conversely, the base heating element 42 is depicted as being mounted to an exterior face of the base 26. It is noted that this configuration is illustrative and non-limiting. That is, it is contemplated that one or more of the heating elements for the cover heating element assembly 44 can be disposed on an exterior face or exterior faces of the cover, while the base heating element 42 can be disposed on the interior face of the base 26.

Furthermore, it is also contemplated that each enclosure portion can be heated with a plurality of heating elements (or, alternatively, a plurality of heating element zones), as depicted in FIG. 2 as 42a, 42b and 42c for the base heating element 42. The same multi-element arrangement, though not depicted, can be implemented on in the heating of the perimeter portion 32 (e.g., using a plurality of heating elements stacked vertically for heating of perimeter portion 32). Each of the heating elements and/or heating zones can be controlled to a set point temperature by the control system 16.

In one embodiment, the temperature of the environment within the enclosure 28 is controlled to a set point. Alternatively, the base heating element 42 and the heating element assembly 44 themselves are controlled to predetermined temperatures. In other embodiments, multi-input control schemes can be utilized, which include inputs from two or more of the internal gas temperature, internal component temperatures, and ambient temperature.

In the depiction of FIG. 2, the "various appurtenances" include mass flow controllers 52, back pressure controller 54, plumbing 56, a gas mixer 58, a check valve 62, various control valves 64, and manual isolation valves 66.

During operation, the base heating element 42 and the heating element assembly 44 are energized under the control of the controller 24 such that the temperature within the chamber becomes elevated relative to the ambient surroundings. The portions of the enclosure 12 that are directly heated (e.g., the perimeter portion 32 and the base 26 for the embodiment depicted in FIGS. 1 and 2) operate at a higher temperature than the unheated portions of the enclosure 12 (i.e., the portions of the enclosure 12 that are not directly heated, represented by the opposing portion 34 of FIGS. 1 and 2). During heater energization, gas within the enclosure that comes into contact with the directly heated surfaces tends to be heated to a temperature that is greater than the average gas temperature within the enclosure. Conversely, gas within the enclosure that comes into contact with the unheated portion tends to be cooled to a temperature that is less than the average gas temperature within the enclosure. The heated gas rises, while the cooled gas cascades downward, setting up a natural convection loop 72 (FIG. 1).

Functionally, the natural convection loop 72 operates to destratify the gas within the enclosure 12. Without this destratification, the gas at the top of the enclosure 12 can run at a substantially higher temperature than the gas at the bottom of the enclosure 12, causing the temperature within the enclosure 12 to vary substantially. The variation in the temperature can induce substantial thermal gradients within the acoustical sensor 14. The destratification functions to mix the gas so that the temperature is substantially uniform (e.g., within ±0.5° C.). The mixed, destratified gas provides a uniform temperature environment that promotes a substantially uniform temperature for the acoustical sensor 14.

It is understood that a "directly heated" surface can be the surface of a heating element (e.g., heating elements 44a through 44e of FIGS. 1 and 2), or the opposing surface of a heated member to which a heater is mounted on the opposing face (e.g., the interior surface of the base 26 to which the base heating element 42 is directly mounted to the exterior (opposing) face). An "unheated surface" is the surface of a member that is not in direct contact with a heating element on either of opposing faces. It is noted that an "unheated surface" will tend to be heated by other heat transfer mechanisms, such as by convection with the internal gases of the enclosure and by peripheral conduction from the heated members of the enclosure.

In one embodiment, the base is estimated to have a height H1 of approximately 65 cm (25¾ in.) and a width W1 of approximately 15 cm (6 in.). Also in this embodiment, the cover is estimated to have a height H2 of approximately 44 cm (17⅜ in.), a width W2 of approximately 14 cm (5¾ in.), and a depth D of approximately 16 cm (6¼ in.). Assuming the cover is wrapped in a thermal insulating material (not depicted) that is approximately 30 mm (⅛ in.) thick and having a thermal conductivity of approximately 0.05 W/m$^2$K, it is estimated that the steady state power needed to maintain a 30° C. differential between the interior of the enclosure and the ambient surroundings is on the order of 50 Watts, assuming a natural convection coupling of approximately 60 Watts between the enclosure and the ambient surroundings. An enclosure of such dimensions and configuration can utilize a peak heating power of 100 Watts and still achieve a reasonable ramp rate of heating from a cold start. The watt density of the corresponding heaters translates to approximately 400 W/m$^2$. Source power for the heaters can range from 24 VDC to 240 VAC sources, depending on the environment and the infrastructure available.

Figure 3:
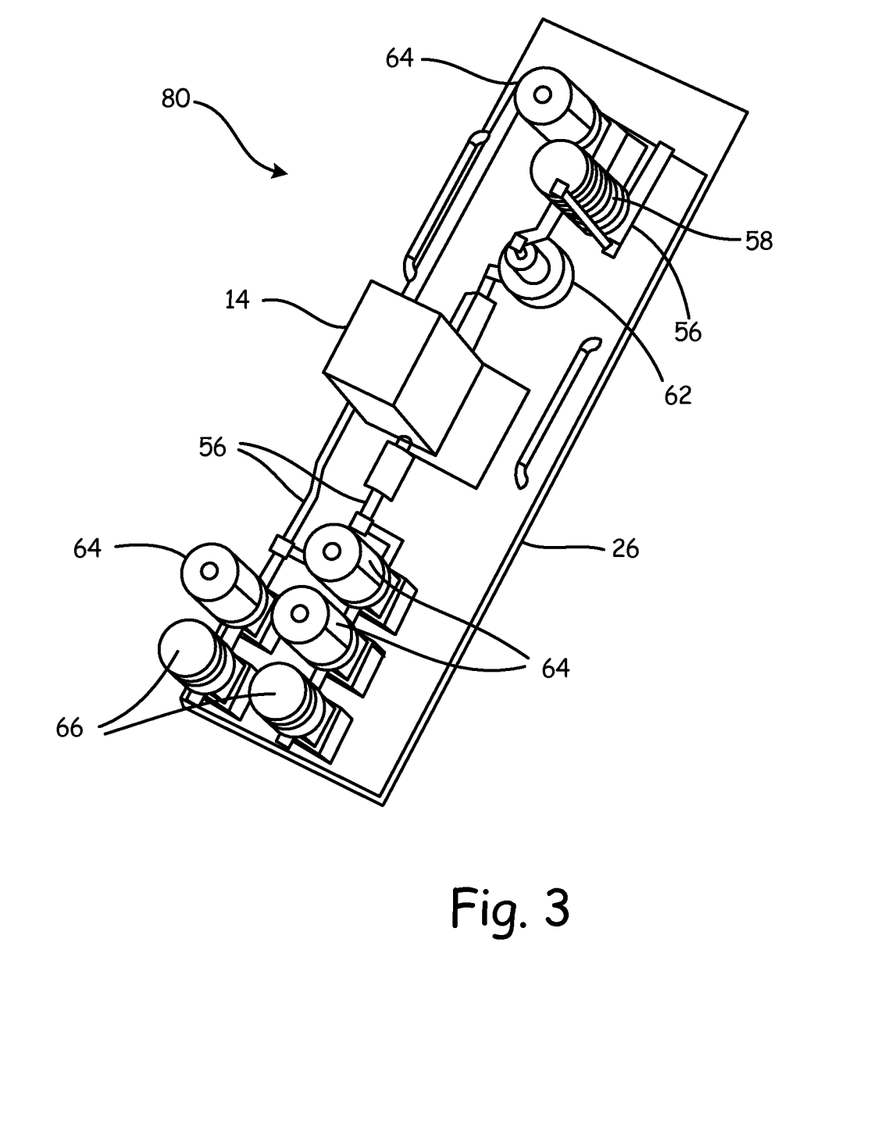
FIG. 3 is a prediction of the temperature of various components within the heated enclosure of FIG. 2 in an embodiment of the disclosure.

Referring to FIG. 3, a temperature distribution 80 of various components within the enclosure 12 of the destratification system 10 is depicted in an embodiment of the invention. The temperature distribution 80 was obtained from a numerical simulation of the destratification system 10, assuming steady state operation with an established convection loop 72. The temperature distribution 80 presents component temperatures having a median temperature of approximately 50° C. and that fall within a ±2° C. range. Note that the temperature of the acoustical sensor appears to be uniform, and that the plumbing 56 in the vicinity of the acoustical sensor 14 appears to be approximately the same. Thus, the numerical simulation indicates that temperature gradients within the acoustical sensor 14 are marginal and that the temperature of the gas entering the acoustical sensor 14 from the plumbing 56 is essentially at equilibrium with the acoustical sensor 14.

Figure 4:
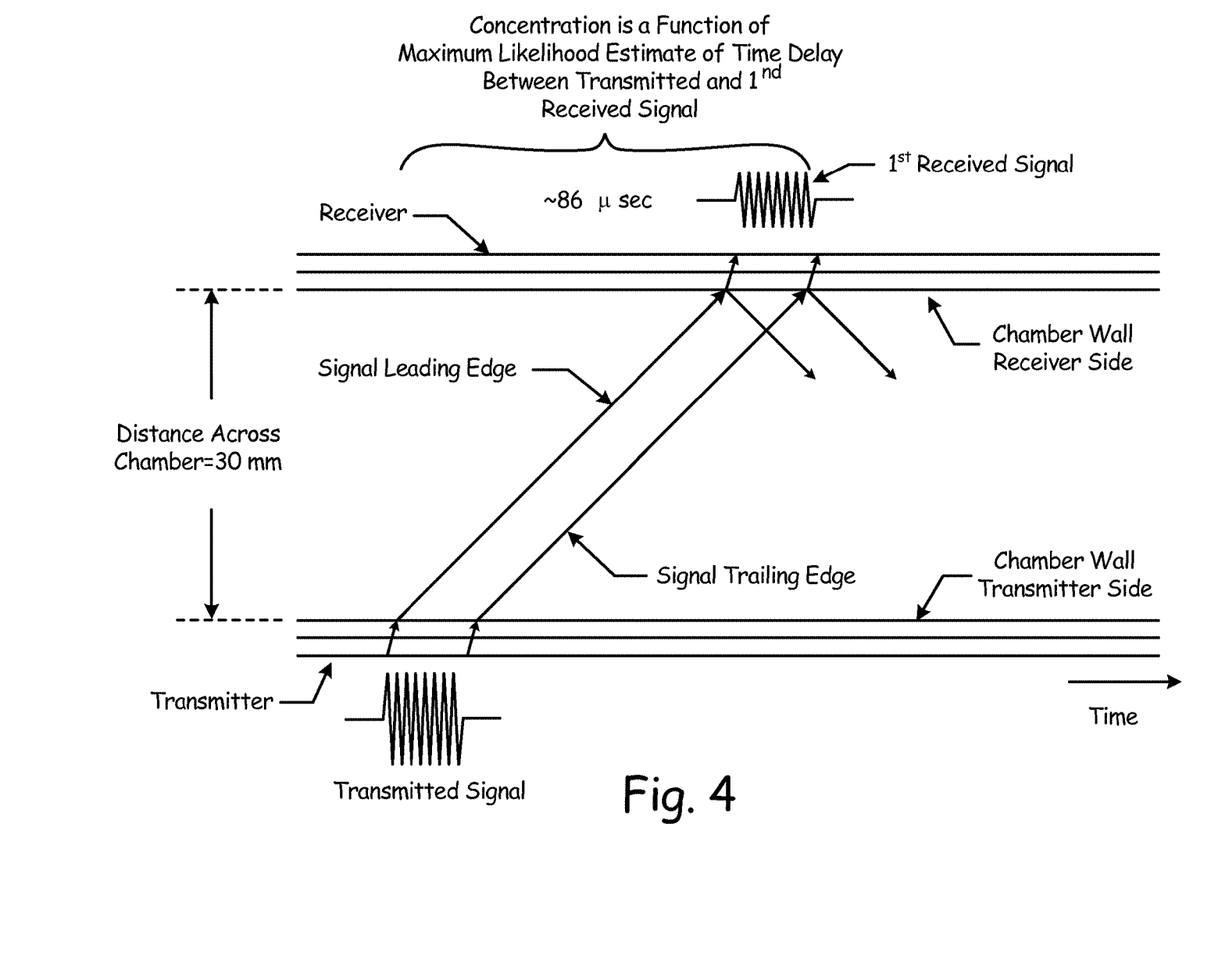
FIG. 4 is a diagram depicting signal propagation across the chamber as a function of time and position according to a measurement arrangement in which a time delay between a transmitted and received signal is determined according to one embodiment.

Related aspects of the acoustical system for measuring material concentration with increased time-of-flight are directed to the acoustical signal itself, as well as reception of the signal. FIG. 4 is a diagram depicting signal propagation across the chamber as a function of time and position. The top and bottom of the diagram represent the receiver and transmitter sides of the chamber, respectively.

The signal has a leading edge, and trailing edge, and consists of a number of cycles within a defined band. In one embodiment, the signal waveform is a single-frequency sinusoid. In another embodiment, the signal waveform includes a chirp portion in which the frequency is swept upwards or downwards at a defined sweep rate. In one example embodiment, from the leading edge, the signal has a continuous-frequency waveform the majority of its duration, followed by an upwardly-swept chirp portion. In a particular implementation, the frequency of the signal is between 2 and 3 MHz.

The received signal consists of the received direct-path signal, having propagated through the chamber. As depicted in FIG. 4, the distance across the chamber is 30 mm in this example. The time between the transmission and reception of the signal is, for the most part, a function of the medium in the chamber (the properties of which establish the propagation speed of the acoustic wave). There are electronic delays associated with the measurement circuitry, which contributes to a lesser extent to the overall delay measurement. Any variability of these electronic delays can contribute to the measurement error. The acoustic wave propagation through the chamber walls is nominal compared to the other factors, and is generally not variable over time. As exemplified in FIG. 4, the measurement arrangement compares the time of the signal transmission against the time of the signal reception. An exemplary time delay of 86 μs for a given medium is represented. This arrangement is susceptible to any electronic delays between the transmitter and receiver circuits affecting the measurement.

Figure 5:
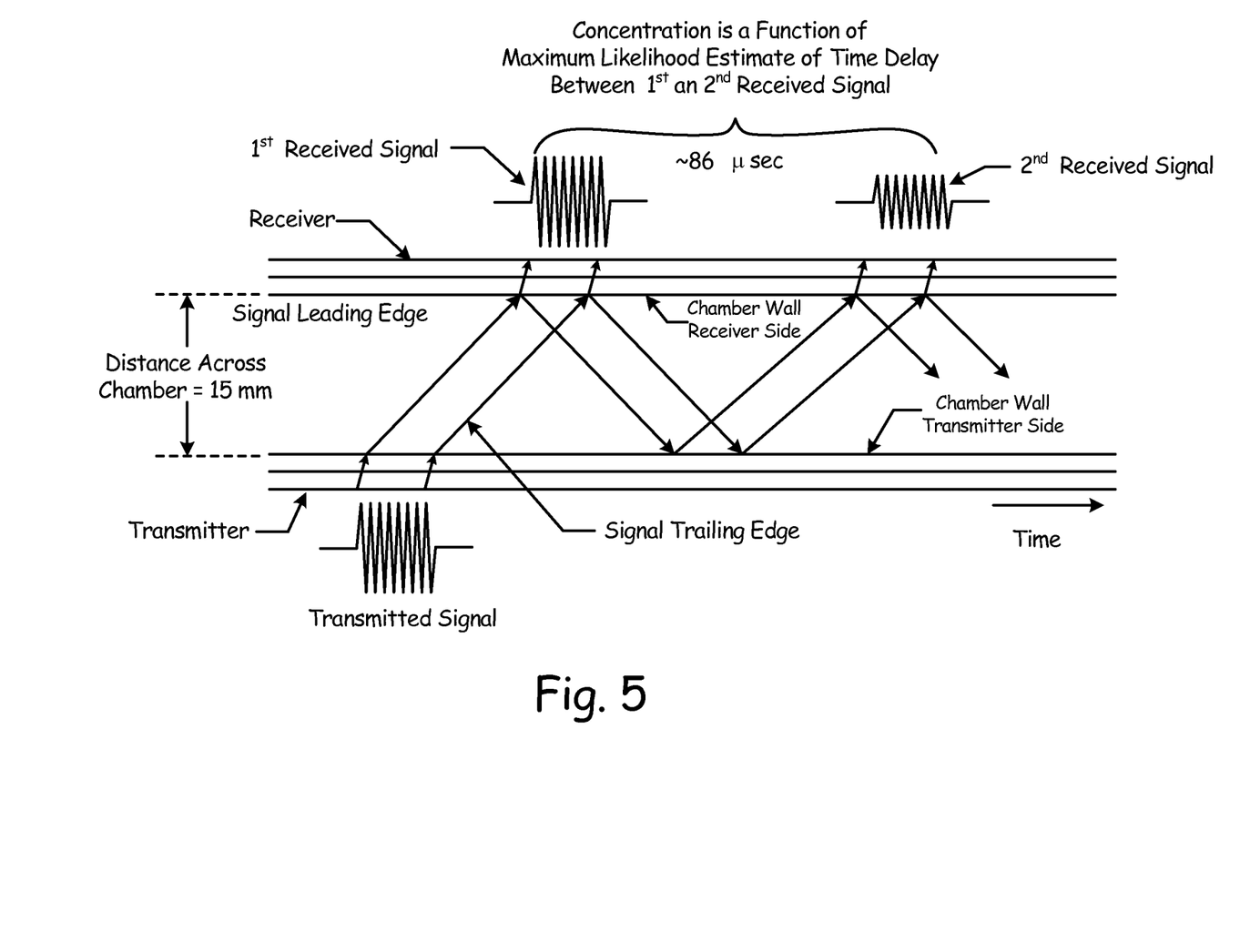
FIG. 5 is a diagram depicting signal propagation across the chamber as a function of time and position according to another measurement arrangement in which a time delay between a first received signal and a second received signal (which is an echo of the first received signal) is determined according to one embodiment.

FIG. 5 illustrates a similar measurement arrangement, which differs primarily in two respects. The chamber is smaller (i.e., the distance from one end to the other for the acoustic wave to traverse) at 15 mm. The other difference is that the delay measurement is made between received signals only. As illustrated, the first received signal is the direct-path signal, having propagated through the chamber from the transmitter. The second received signal consists of the same transmitted wave, having reflected from the receiver-side chamber wall, and the transmitter-side chamber wall. Therefore, the second received signal represents end-to-end travel of the acoustic wave twice through the chamber. Accordingly, the same approximate time delay of 86 μs is exemplified between the compared signals. This measurement arrangement avoids the electronic delay effect between the transmitter and receiver circuits since the transmitter is factored out. The receiver's time delay is constant for both, the first, and the second, received signals. One trade-off in this arrangement compared to the one depicted in FIG. 4 is the additional attenuation of the signal as the wave propagates to produce the second received signal through a greater distance.

Figure 6:
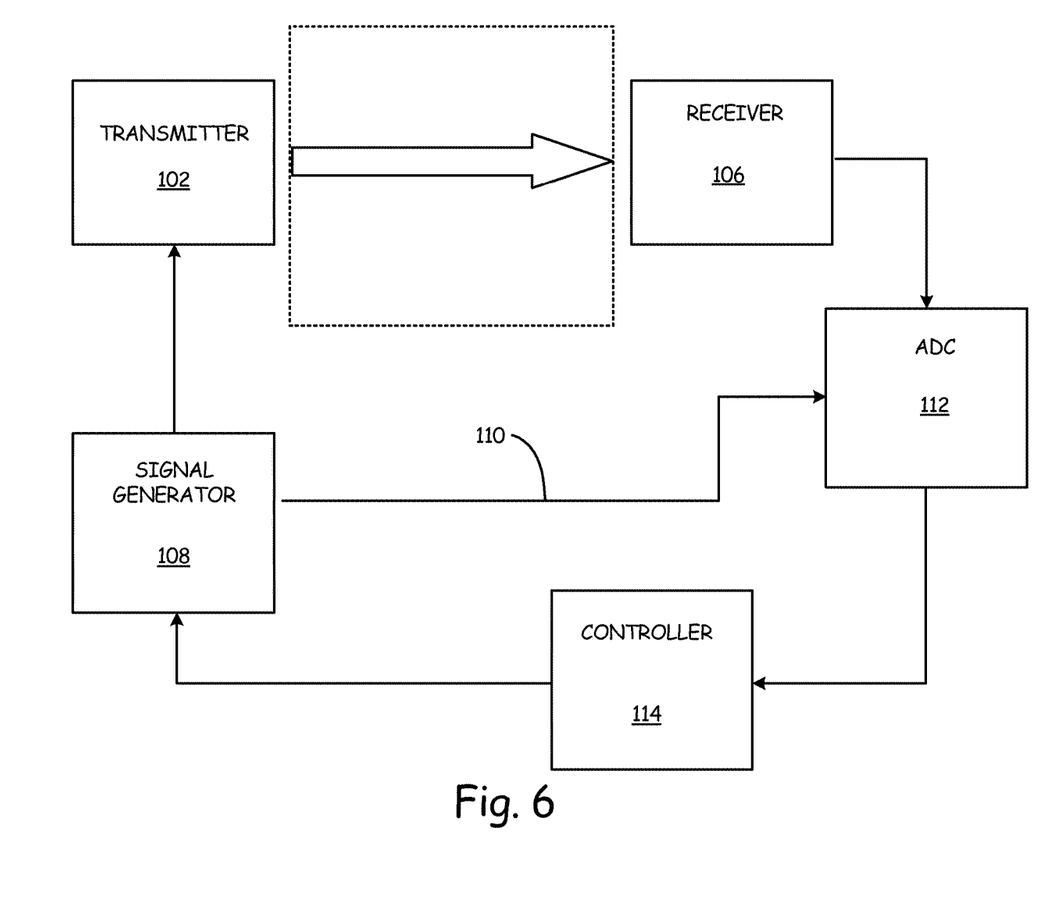
FIG. 6 is a block diagram illustrating a system constructed to implement the measurement arrangements described above with respect to FIG. 4 and FIG. 5, according to one embodiment.

FIG. 6 is a block diagram illustrating a system constructed to implement the measurement arrangements described above with respect to FIG. 4 and FIG. 5, according to one embodiment. Transmitter 102 includes an ultrasonic transducer and driving circuitry. Transmitter 102 produces acoustical signal 104, which is directed to propagate through the chamber 105, to receiver 106. Receiver 106 includes a transducer, which senses the acoustical signal 104 and converts it into an electrical signal, amplifies the electrical signal and filters the signal as needed.

The received signal is outputted to analog-to-digital converter (ADC) 112 to be sampled, quantized, and encoded for use by controller 114. Controller 114 includes a processor-based computer system that can include a microprocessor, digital signal processor (DSP), memory devices, input/output hardware, as well as program instructions for controlling signal generator 108, and analyzing the received signal to determine the propagation time.

The acoustical signal is produced by transmitter 102 from an electrical signal that is generated by signal generator 108. In the embodiment depicted, a reference signal 110 is provided to ADC 112 and ultimately, to controller 114 to be used as a time reference against which the received signal can be compared for the measurement arrangement of FIG. 4. In the measurement arrangement of FIG. 5, the reference signal is obtained from the first received signal.

In various embodiments, signal generator 108 is configured to generate a particular wave form, such as a sinusoidal signal or other suitable waveshape, e.g., square, trapezoidal, etc. at a specific frequency, and for a specific duration. In a related embodiment, the signal is a spread spectrum signal such as a linear chirp where frequency of the transmitted signal is linearly increased (or decreased) by, e.g., 5 to 30%.

In one example embodiment, the signal frequency is between 2 and 3 MHz, and the signal duration is set to produce between 15 and 50 cycles. One particular embodiment uses a signal duration to produce 30 cycles of the generated signal. In a related embodiment, the generated signal is a chirp signal in which the frequency is modulated. For instance, the frequency can be swept upwards or downwards for at least a portion of the signal, such as over the lest several cycles.

In a related embodiment, ADC 112 is configured to substantially oversample the received signal. For example, sampling at a rate of 32 samples per cycle (which in this case is oversampling of 16 times the Nyquist rate) is employed. In various other embodiments, it is contemplated that sampling at rates ranging from 20-200 or more samples per cycle may be utilized, according to the processing capability of controller 114.

In one type of embodiment, controller 114 is programmed to implement a maximum-likelihood (ML) estimation algorithm to determine the time delay associated with signal propagation through the chamber. ML estimation is well-known, and described in Fisher, R. A., On an Absolute Criterion for Fitting Frequency Curves, Mess. of Math., 41, pp. 155-160, 1912, and Van Trees, Harry L., Detection, Estimation, and Modulation Theory, Part 1., John Wiley & Sons, Inc., New York, 1968, both references being incorporated by reference herein.

For the measurement arrangement of FIG. 4, the ML function of the transmitted and received signals is computed, and the measured concentration is a function of the number of samples (and fractional samples, if any) between the peaks or other feature in the ML functions of the transmitted and received signals. For the measurement arrangement of FIG. 5, the ML function of the first received and second received signals is computed, and the measured concentration is a function of the number of samples (and fractional samples, if any) between the peaks in the ML functions of the first received signal and the second received signal.

Another system that can be incorporated into enclosure 12 is a low concentration gas delivery system. For some process steps in MOCVD and atomic layer deposition (ALD) systems, not only is it desirable to accurately detect low concentrations of a constituent, such as $Cp_2Mg$ (i.e., bis cyclopentadienyl magnesium—having molecular formula $(C_5H_5)_2Mg$), it is also important to deliver a prescribed mass transfer rate (e.g., molecules per second), which is sometimes constant but often varied during the deposition step, of a low concentration constituent to an MOCVD or ALD reactor to ensure that the appropriate amount of doping or layer formation occurs when a semiconductor device is grown in the MOCVD or ALD reactor.

Figure 7:
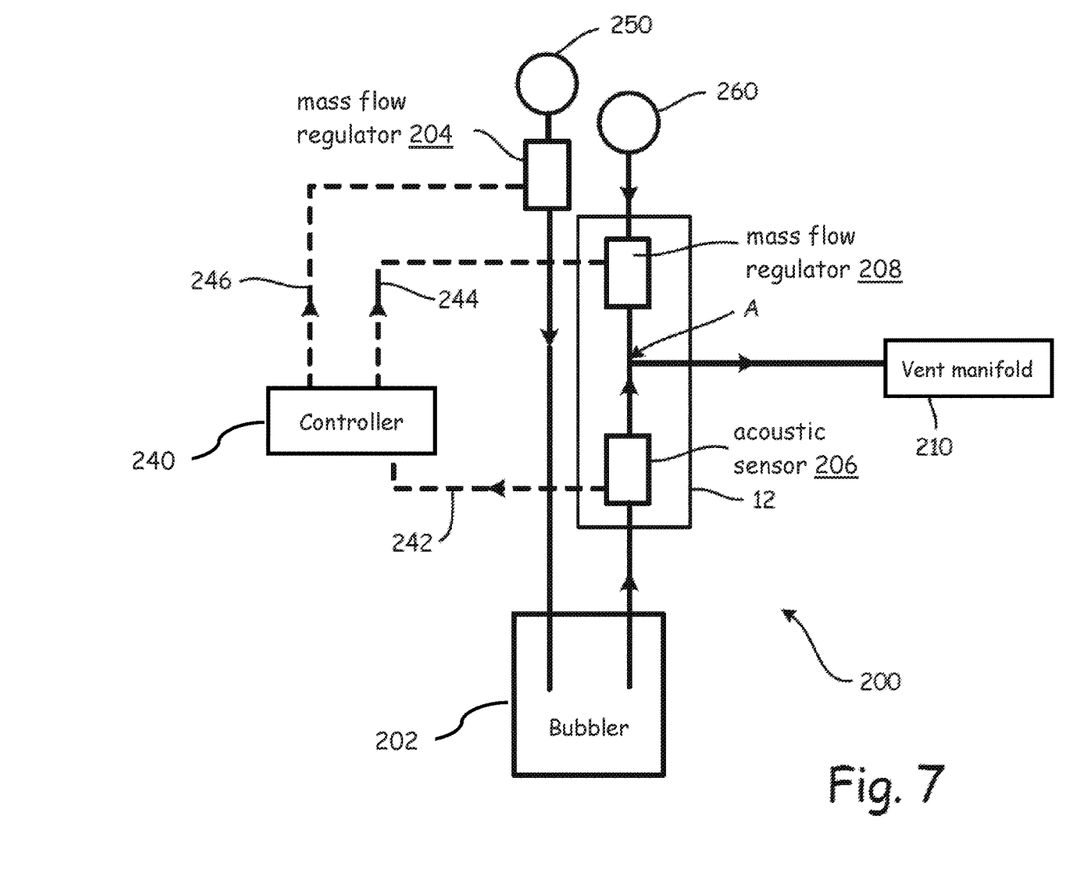
FIG. 7 is a schematic diagram illustrating system to deliver a prescribed mass transfer rate of a low concentration constituent to a process chamber according to one embodiment.

A system to deliver a prescribed mass transfer rate of a low concentration constituent to a process chamber such as a MOCVD or ALD reactor according to one embodiment is illustrated in FIG. 7. As depicted, low concentration constituent delivery system 200 has a bubbler 202 which contains a precursor process source. Examples of suitable bubblers include those shown in US Published Patent Application 20070221127, U.S. Pat. No. 5,603,169, and U.S. Pat. No. 6,561,498, the contents of which are hereby incorporated by reference herein. In general, bubbler 202 includes a precursor vessel that has an inlet for the carrier gas, and an outlet that carries a precursor gas-carrier gas mixture.

The precursor process source can be, for example, $Cp_2Mg$, trialkyl aluminum (for example, trimethyl aluminum), trialkyl gallium (for example, triethyl gallium, trimethyl gallium), trialkyl antimony, dimethyl hydrazine, trialkyl indium (for example, trimethyl indium), TDMAT (tetrakis (dimethylamido) titanium), PDMAT (pentakis (dimethylamido) tantalum) and other metallo-organic compounds typically used in MOCVD and ALD processes.

An inert carrier gas for the precursor process source, for example, nitrogen, hydrogen, helium, argon, and the like, from inert carrier gas source 250 is charged into bubbler 202, the flow of which is monitored by mass flow regulator 204.

Bubbler 202, which may have a heating source (not shown), facilitates mixing of vapors of the precursor process source and inert carrier gas. The inert carrier gas containing precursor process source then flows out of bubbler 202 and passes into acoustic sensor 206 (similar to acoustical sensor 14 discussed hereinabove). Acoustical sensor 206, mass flow regulator 208, and dilution point A (which can be a T joint or a static mixer) are placed within enclosure 12, the benefits of which are discussed above.

For low vapor pressure precursor process sources such as $Cp_2Mg$, it is sometimes advantageous to increase the temperature of the bubbler 202 to above ambient temperature (e.g. to at or about 50° C.) to increase the precursor concentration as it exits bubbler 202. An increased precursor concentration can provide a more repeatable and accurate concentration measurement by acoustic sensor 206. As discussed below, a dilution gas is then mixed with the gas mixture exiting acoustic sensor 206 and prior to exiting the heated enclosure 12 at dilution point A to allow the output mixture to be delivered to reactor or vent manifold 210 at ambient temperature (e.g. at or about 25° C.). In this manner, condensation of precursor process source can be avoided in the gas lines that subsequently feed to the reactor, ensuring that the proper mass transfer rate of precursor process source is delivered to the reactor and any potential damage to the gas lines due to condensation can be avoided or at least reduced to a negligible level.

A dilution gas, for example, nitrogen, hydrogen, helium, argon, and the like, flows from dilution gas source 260 into mass flow regulator 208.

The inert carrier gas containing precursor process source flowing out of acoustic sensor 206 and dilution gas flowing out of mass flow regulator 208 meet at dilution point A forming a gas mixture, where a suitable network of piping and valves (details omitted for clarity) direct the gas mixture to flow to reactor/vent manifold 210.

As the inert carrier gas containing precursor process source flows through acoustical sensor 206, acoustical sensor 206 measures the precursor process source concentration as discussed above with reference to FIG. 6.

The precursor process source concentration as determined by acoustical sensor 206 is then fed into controller 240. Controller 240 includes actuators and, optionally, additional sensors, that are each interfaced with a processor-based control system that include a microprocessor or digital signal processor (DSP), memory devices, input/output hardware, as well as program instructions stored on the memory devices and executable on the microprocessor or DSP for determining the mass transfer rate of the precursor needed for reactor/vent manifold 210, along with program instructions for actuating mass flow regulators 204 and 208.

When the program instructions for determining the mass transfer rate of the precursor are activated, since the concentration and flow rate of the inert carrier gas containing precursor process source is known, the precursor mass transfer rate reaching reactor/vent manifold 210 can be adjusted by sending an appropriate signal from controller 240 to mass flow regulator 204 via connection 246 and/or by sending an appropriate signal from controller 240 to mass flow regulator 208 via connection 244. The signals sent by controller 240 to mass flow regulator 204 and/or mass flow regulator 208 controls the amount of carrier gas feeding into mass flow regulator 204 and/or the dilution gas feeding into mass flow regulator 208.

The program instructions in controller 240 take into account the distance from acoustic sensor 206 to dilution point A and from dilution point A to reactor/vent manifold 210 such that the precursor mass transfer rate versus time is maintained at the desired profile independent of precursor concentration exiting the bubbler. In a related embodiment, the flow rate through the bubbler 202 is increased or decreased depending upon whether there is a ramp up or ramp down of precursor mass transfer rate that is needed for the reactor during a deposition step (for example, when providing a graded doping profile of $Cp_2Mg$ when growing a p-GaN layer in the fabrication of a light emitting diode).

The gas mixture flowing towards reactor/vent manifold 210, in configurations where element 210 is a reactor, can optionally be further mixed with a push gas (for example, nitrogen, hydrogen, helium, argon, and the like) to increase the speed at which the gas mixture reaches the reactor 210.

When reactor/vent manifold 210 is set to a vent state, calibration of acoustic sensor 206 can be done (with mass flow regulator 208 preventing dilution supplied by dilution gas source 260 from entering dilution point A) using a suitable procedure.

All of the features disclosed in this specification (including any accompanying claims, abstract and drawings), and/or all of the steps of any method or process so disclosed, can be combined in any combination, except combinations where at least some of such features and/or steps are mutually exclusive.

Each feature disclosed in this specification (including any accompanying claims, abstract and drawings) can be replaced by alternative features serving the same, equivalent or similar purpose, unless expressly stated otherwise. Thus, unless expressly stated otherwise, each feature disclosed is one example only of a generic series of equivalent or similar features.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. An apparatus for acoustically determining a property of a test medium, comprising:
    an enclosure including a base and a cover, said base and said cover cooperating to define a chamber;
    an acoustical sensor mounted to said base, said acoustical sensor including a first acoustical transducer defining a first exposed face and a second acoustical transducer defining a second exposed face, said first exposed face and said second exposed face being substantially parallel and adapted for contact with said test medium and defining a gap therebetween;
    at least one heating element operatively coupled with said enclosure, wherein a first portion of said enclosure is operatively coupled with said at least one heating element, said first portion extending along a height of a natural convection loop, wherein a second portion of said enclosure is not operatively coupled with said at least one heating element, said second portion extending along the height of the natural convection loop, the second portion opposing said first portion of said enclosure to create the natural convection loop within the enclosure that mixes the gases and provides destratification.

2. The apparatus of claim 1, wherein said second portion of said enclosure is operatively coupled to a cooling device, and wherein said cooling device includes a plurality of cooling fins.

3. The apparatus of claim 1, wherein said first portion of said enclosure is said base.

4. The apparatus of claim 1, wherein:
said enclosure substantially defines a rectangular box, said cover defining a top portion, a bottom portion, a first side portion, a second side portion and a third side portion, said second side portion being adjacent to and disposed between said first side portion and said third side portion;
said second portion of said enclosure is said second side portion.

5. The apparatus of claim 1, wherein said acoustical sensor is oriented so that said first exposed face of said first acoustical transducer and said second exposed face of said second acoustical transducer face horizontally.

6. The apparatus of claim 1, wherein said gap is greater than 12 mm and less than 50 mm.

7. The apparatus of claim 6, wherein said gap is approximately 15 mm.

8. The apparatus of claim 6, wherein said gap is approximately 30 mm.

9. An apparatus for acoustically determining a property of a test medium, comprising:
an enclosure including a base and a cover, said base and said cover cooperating to define a chamber;
an acoustical sensor mounted to said base, said acoustical sensor including a first acoustical transducer defining a first exposed face and a second acoustical transducer defining a second exposed face, said first exposed face and said second exposed face being parallel and adapted for contact with said test medium and defining a gap therebetween;
at least one heating element operatively coupled with said enclosure,
wherein a first portion of said enclosure is operatively coupled with said at least one heating element, said first portion being vertically oriented,
wherein a second portion of said enclosure is not operatively coupled with said at least one heating element, said second portion being vertically oriented and opposing said first portion of said enclosure,
wherein said at least one heating element substantially surrounds said acoustical sensor.

10. A method of maintaining an acoustical sensor at a substantially uniform temperature, comprising:
providing an acoustical sensor mounted within an enclosure, said acoustical sensor including first and second acoustical transducers that are substantially parallel to each other and adapted for contact with a test medium, said first and second acoustical transducers defining a gap therebetween;

providing a heating system adapted to apply heat to portions of said enclosure, said portions substantially surrounding said acoustical sensor; and
providing a set of instructions on a tangible medium, said instructions comprising:
heating portions of said enclosure that substantially surround said acoustical sensor;
cooling a substantially vertical portion of said enclosure to induce a recirculation of a gas within said enclosure, said recirculation causing destratification of said gas within said enclosure.

11. The method of claim 10, wherein said destratification of said gas causes a spatial temperature variation of said gas within said enclosure to be within a predetermined value.

12. The method of claim 10, wherein the step of cooling a substantially vertical portion of said enclosure includes free convection between said substantially vertical portion of said enclosure and ambient surroundings.

13. The method of claim 10, wherein the step of heating portions of said enclosure include controlling the temperature of said portions to a set point that is at least 20° C. greater than an ambient temperature that surrounds said enclosure.

14. An apparatus for acoustically determining a property of a test medium, comprising:
an enclosure including a base and a cover, said base and said cover cooperating to define a chamber;
an acoustical sensor mounted to said base, said acoustical sensor including a first acoustical transducer defining a first exposed face and a second acoustical transducer defining a second exposed face, said first exposed face and said second exposed face situated in a facing arrangement with one another and being constructed to contact said test medium and define a gap therebetween;
said first acoustical transducer being electrically coupled with a transmitter circuit constructed to actuate said first acoustical transducer by a first generated signal having a frequency of between 2 and 3 MHz and a duration of between 15 and 50 cycles to produce a first acoustical signal directed to travel through said gap;
said second acoustical transducer being electrically coupled with a receiver circuit constructed to produce a first received signal from the first acoustical signal;
said receiver circuit being electrically coupled to a digitizing circuit configured to sample the first received signal at a sampling rate of between 20 and 100 samples per cycle to produce a first received digital signal;
said digitizing circuit being electrically coupled to a controller circuit that includes a processor and a non-transitory data storage medium containing instructions that, when executed, cause the processor to apply a maximum-likelihood function to the first received digital signal and to a reference digital signal, and to determine a time delay between a feature of the first received digital signal and a feature of the reference digital signal, said time delay between features being indicative of property of said test medium.

15. A mass-transfer rate control arrangement comprising:
a carrier gas source;
a carrier gas mass flow regulator arranged to regulate a rate of flow of carrier gas from the carrier gas source;
a process precursor source, including a precursor vessel having an inlet in fluid communication with the carrier gas source via the carrier gas mass flow regulator, and an outlet arranged to convey a mixture of the process precursor and the carrier gas;

an acoustical sensor in fluid communication with the outlet, the acoustical sensor comprising a chamber arranged to convey a flow of the mixture through the chamber, and further comprising an electrical signal generator constructed to generate an electrical signal representing a quantity of the process precursor present in the mixture flowing through the chamber;

a dilution gas source;

a dilution gas mass flow regulator arranged to regulate a rate of flow of the dilution gas from the dilution gas source, the dilution gas source being in fluid communication with the outlet of the precursor vessel via the dilution gas mass flow regulator, wherein the fluid communication of the dilution gas source and the outlet of the precursor vessel includes a dilution point at which a diluted mixture of the dilution gas and the process precursor-carrier gas mixture is achieved; and a controller electrically coupled with at least one of the carrier gas mass flow regulator, the dilution gas mass flow regulator, and with the acoustical sensor, the controller being configured to adjust at least one of the carrier gas mass flow regulator and the dilution gas mass flow regulator in response to the electrical signal from the acoustical sensor such that the diluted mixture at the dilution point has a prescribed mass transfer rate.

16. A mass-transfer rate control arrangement of claim 15, wherein the dilution gas source is in fluid communication with the outlet of the precursor vessel via the dilution gas mass flow regulator downstream of the acoustical sensor.

17. A mass-transfer rate control arrangement of claim 15, wherein the dilution point is fluidly coupled with a vent manifold.

18. A mass-transfer rate control arrangement of claim 15, wherein the dilution point is fluidly coupled with a process reactor.

19. A mass-transfer rate control arrangement of claim 15, wherein the controller is electrically coupled with both, the carrier gas mass flow regulator, and the dilution gas mass flow regulator, and wherein the controller is configured to adjust the carrier gas mass flow regulator and the dilution gas mass flow regulator.

20. A method for controlling a mass-transfer rate within a process gas mixture, the method comprising:

providing a carrier gas;

providing a process precursor gas;

producing a process precursor mixture containing the carrier gas and a process precursor gas;

acoustically sensing a quantity of the process precursor present in the process precursor mixture to produce a sensor output;

providing a dilution gas;

conveying the process precursor mixture and separately conveying the dilution gas to a dilution point at which a diluted mixture of the dilution gas and the process precursor mixture is achieved; and automatically controlling a relative flow rate of the carrier gas and the dilution gas in response to the sensor output such that the diluted mixture at the dilution point has a prescribed mass transfer rate of the precursor gas.

* * * * *